(12) United States Patent
Liu et al.

(10) Patent No.: US 12,073,539 B2
(45) Date of Patent: Aug. 27, 2024

(54) SYSTEMS AND METHODS FOR DENOISING MEDICAL IMAGES

(71) Applicant: Shanghai United Imaging Intelligence Co., Ltd., Shanghai (CN)

(72) Inventors: Yikang Liu, Cambridge, MA (US); Shanhui Sun, Lexington, MA (US); Terrence Chen, Lexington, MA (US); Zhang Chen, Brookline, MA (US); Xiao Chen, Cambridge, MA (US)

(73) Assignee: Shanghai United Imaging Intelligence Co., Ltd., Shanghai (CN)

( * ) Notice: Subject to any disclaimer, the term of this patent is extended or adjusted under 35 U.S.C. 154(b) by 440 days.

(21) Appl. No.: 17/564,348

(22) Filed: Dec. 29, 2021

(65) Prior Publication Data
US 2023/0206401 A1  Jun. 29, 2023

(51) Int. Cl.
| | |
|---|---|
| *G06K 9/62* | (2022.01) |
| *G06N 3/045* | (2023.01) |
| *G06N 3/08* | (2023.01) |
| *G06T 5/50* | (2006.01) |
| *G06T 5/70* | (2024.01) |
| *G16H 30/40* | (2018.01) |

(52) U.S. Cl.
CPC ............... *G06T 5/70* (2024.01); *G06N 3/045* (2023.01); *G06N 3/08* (2013.01); *G06T 5/50* (2013.01); *G16H 30/40* (2018.01); *G06T 2207/10064* (2013.01); *G06T 2207/20081* (2013.01); *G06T 2207/20084* (2013.01)

(58) Field of Classification Search
CPC ... G06T 5/70; G06T 5/50; G06T 2207/10064; G06T 2207/20081; G06T 2207/20084; G06T 5/60; G06N 3/045; G06N 3/08; G16H 30/40
See application file for complete search history.

(56) References Cited

U.S. PATENT DOCUMENTS

| | | | |
|---|---|---|---|
| 8,605,970 B2 | 12/2013 | Bar-Aviv et al. | |
| 10,685,429 B2 * | 6/2020 | Mentl | G06T 11/008 |
| 10,949,951 B2 | 3/2021 | Tang et al. | |
| 2018/0089807 A1 | 3/2018 | Reusch et al. | |

(Continued)

FOREIGN PATENT DOCUMENTS

| | | | |
|---|---|---|---|
| CN | 106600568 B | 10/2019 | |
| CN | 111199526 A | 5/2020 | |
| CN | 113344799 A * | 9/2021 | ........... A61B 6/5258 |

(Continued)

*Primary Examiner* — Xin Jia
(74) *Attorney, Agent, or Firm* — Zhong Law, LLC (57) ABSTRACT

Described herein are systems, methods, and instrumentalities associated with denoising medical images such as fluoroscopic images using deep learning techniques. A first artificial neural network (ANN) is trained to denoise an input medical image in accordance with a provided target noise level. The training of the first ANN is conducted by pairing a noisy input image with target denoised images that include different levels of noise. These target denoised images are generated using a second ANN as intermediate outputs of the second ANN during different training iterations. As such, the first ANN may learn to perform the denoising task in an unsupervised manner without requiring noise-free training images as the ground truth.

20 Claims, 6 Drawing Sheets

(56) References Cited

U.S. PATENT DOCUMENTS

2021/0264573 A1    8/2021  Tamal et al.
2021/0383510 A1*  12/2021  Sharma .................... G06T 5/70

FOREIGN PATENT DOCUMENTS

CN         113344811  A        9/2021
JP         2019069145 A   *    5/2019   ........... A61B 5/0035
WO    WO-2022076654 A1  *    4/2022   ............. G01R 33/56

* cited by examiner

SYSTEMS AND METHODS FOR DENOISING MEDICAL IMAGES

BACKGROUND

Medical images are usually noisy due to constraints imposed upon the imaging process and/or the target objects such as acquisition times, radiation dosage, spatial resolutions, etc. Various techniques have been developed for denoising medical images. But since different medical images may include different levels of noises (e.g., varying signal-to-noise ratios (SNRs)), it is difficult to develop a universal denoising method. Moreover, even though machine learning (ML) has shown great promises in the field of image processing, difficulties in obtaining noise-free medical images have rendered supervised machine learning techniques that require having noise-free medical images as the ground truth impractical for medical image denoising. As a result, it is highly desirable to develop machine learning based systems and methods that not only are capable of processing medical images with varying noise levels but also do not require supervised training or noise-free medical images as the ground truth.

SUMMARY

Described herein are systems, methods, and instrumentalities associated with denoising medical images such as fluoroscopic images. An apparatus configured to perform the denoising tasks described herein may include one or more processors that may be configured to receive an input medical image comprising noise, receive a target noise level (e.g., corresponding to a target signal-to-noise ratio (SNR)), and generate an output medical image using a first artificial neural network (ANN) such that at least a portion of the noise is removed from the output medical image in accordance with the target noise level. The first ANN may be trained to generate the output medical image in accordance with the target noise level through a training process. During the training process, the first ANN may be configured to receive a first pair of training images that may include a first noisy training image and a first target training image, wherein the first target training image may be generated using a second ANN and may include a first level of noise. The first ANN may be configured to determine the first level of noise associated with the first target training image, generate a denoised version of the first noisy training image using the first ANN based on the first level of noise, and adjust parameters of the first ANN based on a difference (e.g., a loss) between the denoised version of the first noisy training image and the first target training image. The first ANN may be further configured to receive a second pair of training images during the training process. The second pair of training images may include a second noisy training image and a second target training image, wherein the second target training image may also be generated using the second ANN and may include a second level of noise. The first ANN may determine the second level of noise associated with the second target training image, generate a denoised version of the second noisy training image using the first ANN based on the second level of noise, and further adjust the parameters of the first ANN based on a difference (e.g., a loss) between the denoised version of the second noisy training image and the second target training image.

In examples, the first noisy training image and the second noisy training image described above may correspond to a same source image, and the first target training image and the second target training image may be generated by the second ANN based on the same source image but with different levels of noise (e.g., the first level of noise may be different than the second level of noise). The second ANN may be pre-trained to denoise the source image through multiple training iterations. During each of the multiple training iterations, the second ANN may be configured to generate a respective intermediate denoised output image with a corresponding noise level based on the source image, wherein the first target training image may be obtained as the intermediate denoised output image generated during a first training iteration of the second ANN and the second target training image may be obtained as the intermediate denoised output image generated during a second training iteration of the second ANN. In examples, the second ANN comprises a convolutional neural network (CNN) trained to predict a pixel value in an output image based on a corresponding pixel in an input noisy image and a plurality of pixels surrounding the corresponding pixel in the input noisy image.

In examples, the first ANN described above may be configured to process multiple input images through respective input channels and the first ANN may be configured to generate the output medical image by obtaining an image having a same size as the input medical image, wherein each pixel of the image is assigned a value indicating the target noise level, and processing the obtained image and the input medical image via respective first input channel and second input channel of the first ANN. In examples, the first ANN may be configured to shuffle the input medical image into a plurality of images each having a smaller image size than the input medical image and process the plurality of images through the respective input channels of the first ANN.

BRIEF DESCRIPTION OF THE DRAWINGS

A more detailed understanding of the examples disclosed herein may be had from the following description, given by way of example in conjunction with the accompanying drawing.

DETAILED DESCRIPTION

The present disclosure is illustrated by way of example, and not by way of limitation, in the figures of the accompanying drawings.

Figure 1:
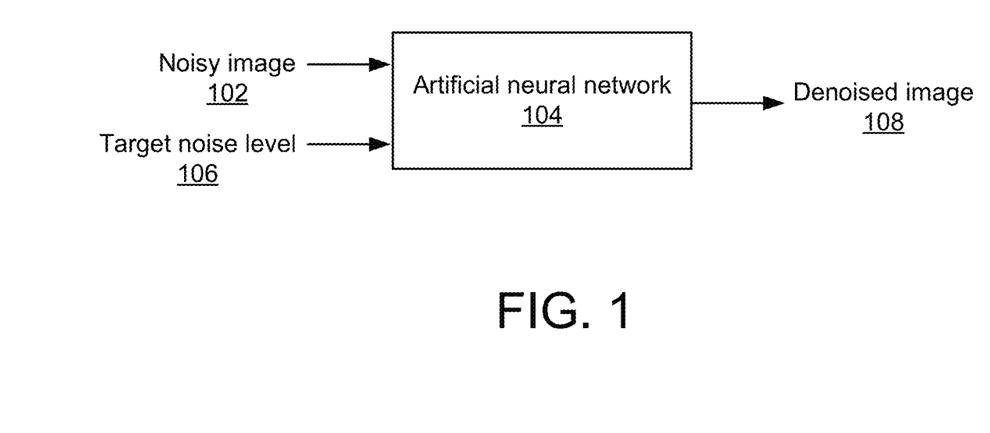
FIG. 1 is a diagram illustrating an example of a neural network system or apparatus that may be used to denoise a medical image based on a target noise level.

FIG. 1 illustrates an example of denoising a medical image (e.g., 102) using an artificial neural network (ANN) (e.g., 104) in accordance with a target noise level (e.g., 106).

Medical image 102 may be a medical image (e.g., a scan image) of different types including, for example, a fluoroscopic image, a magnetic resonance imaging (MRI) image, a computer tomography (CT) image, etc. Because of various conditions or constraints associated with the imaging process and/or the object shown in the image, medical image 102 may include a certain amount of noise that may affect the quality (e.g., clarity, sharpness, etc.) of the image. ANN 104 may be configured to implement an image denoising model (e.g., a machine learned (ML) model) to remove at least a portion of the noise included in medical image 102 based on target noise level 106 and generate an output medical image (e.g., 108) in which the level of noise is reduced to target noise level 106.

Target noise level 106 may be preconfigured (e.g., preset) for a denoising system or apparatus configured to implement denoising model 104. Target noise level 106 may also be received (e.g., in real time) from a user (e.g., via a user interface) or from an external device (e.g., via a communication interface). In any event, a lower target noise level may cause denoising model 104 to generate an output medical image that is shaper (e.g., including more high frequency components) but noisier (e.g., including more artifacts), whereas a higher target noise level may cause denoising model 104 to generate an output medical image that is blurrier (e.g., including fewer high frequency components) but cleaner (e.g., including fewer artifacts). In examples, a machine learning model may be trained to predict (e.g., based on noisy image 102) a value for target noise level 106 that may balance between the sharpness and the amount of noise in the output image (e.g., to predict a sweet spot between a high image sharpness and a low number of noise artifacts). In examples, target noise level 106 may represent or correspond to a signal-to-noise ratio (SNR).

ANN 104 may be trained to learn the denoising model (e.g., which may be realized through the parameters or weights of ANN 104) through a training process. The training may be conducted using an instance of the ANN (e.g., a first ANN) and as will be described in greater detail below, the training of the ANN may be conducted utilizing images generated by another ANN (e.g., a second ANN), thus eliminating the need for noise-free images. In examples, either or both of the first ANN and the second ANN may include a convolutional neural network (CNN) such as a fully convolutional neural network. The CNN may be trained to learn a mapping (e.g., a mathematical mapping) between noisy medical images and target clean (e.g., less noisy) medical images based on information redundancy (e.g., statistical dependency) among pixels of the medical images. In examples, the CNN may be an encoder-decoder network (e.g., having a U-Net structure) that may include multiple convolutional layers and/or one or more pooling layers. The convolutional layers may be followed by batch normalization and/or linear or non-linear activation (e.g., such as rectified linear unit or ReLU activation), and each of the convolutional layers may include a plurality of convolution kernels or filters having respective weights, the values of which may be learned through the training process described above so as to extract features from an input image. The features extracted by the convolutional layers may be down-sampled through one or more pooling layers to obtain a representation of the features, for example, in the form of a feature map or feature vector. The CNN may further include one or more un-pooling layers and one or more transposed convolutional layers. Through the un-pooling layers, the CNN may up-sample the features extracted from the input images and further process the up-sampled features through the one or more transposed convolutional layers (e.g., via a plurality of deconvolution operations) to derive an up-scaled (e.g., dense) feature map or feature vector. The up-scaled feature map or vector may then be used to predict pixel values in an output image (e.g., output image 108) that are free of certain noise (e.g., in accordance with target noise level 106).

Figure 2:
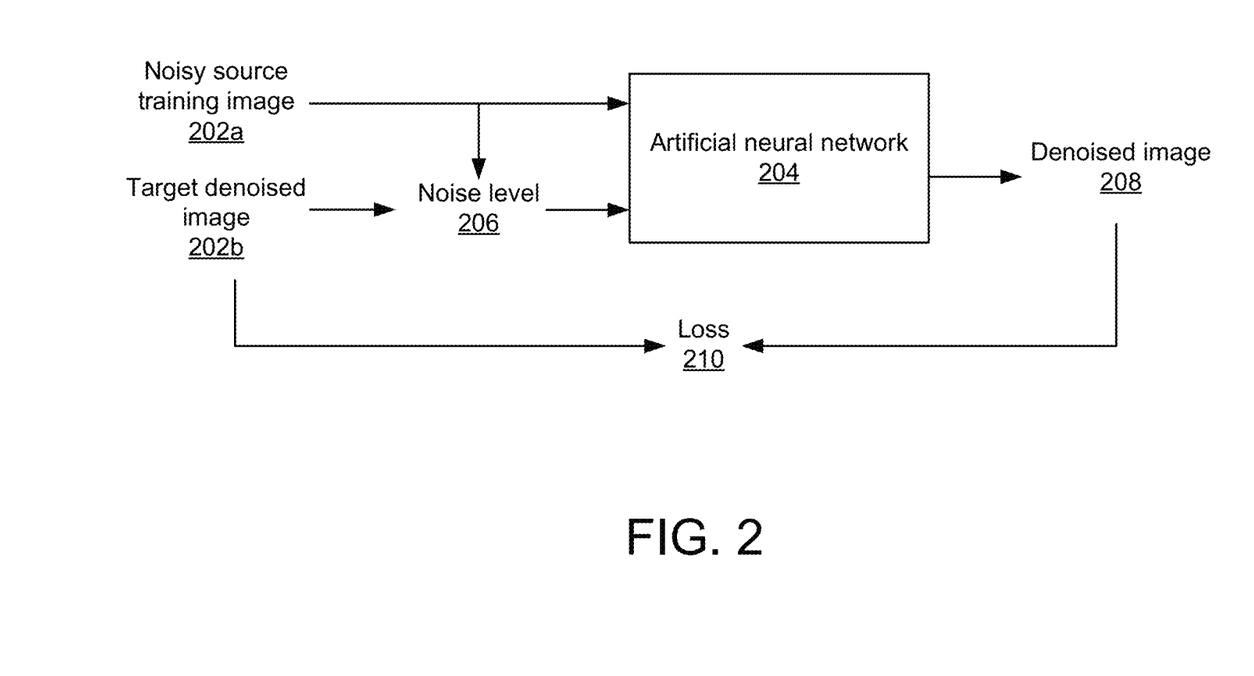
FIG. 2 is a diagram illustrating example operations that may be associated with the training of the neural network of FIG. 1.

FIG. 2 illustrates example operations that may be associated with training an ANN (e.g., ANN 104 of FIG. 1) to learn the denoising model described herein. As shown, the training may be conducted using paired training images. Each pair of such training images may include a noisy source training image 202a (e.g., a first noisy training image) and a target denoised image 202b (e.g., a first target training image), with respective levels of noise. During the training (e.g., during a training iteration), the level of noise (e.g., noise level 206) included in target denoised image 202b may be determined, for example, by comparing source training image 202a with target denoised image 202b. For instance, noise level 206 may be determined by subtracting target denoised image 202b from source training image 202a to obtain a noise component and dividing the power of target denoised image 202b by that of the noise component to obtain the noise level (e.g., as an SNR measurement) of target denoised image 202b. The determined noise level (e.g., noise level 206) and source training image 202a may be provided to ANN 204 to predict a denoised output image (e.g., denoised image 208) with a level of noise that approximates noise level 206. ANN 204 may then compare the predicted denoised output image (e.g., image 208) with the target denoised image (e.g., image 202b) and determine a loss (e.g., difference) between the two images. The loss (e.g., loss 210) may be determined using various types of loss functions including, for example, a mean squared error (MSE) based loss function or a structural similarity index (SSIM) based loss function. Once determined, the loss may be used to adjust the parameters of ANN 204 (e.g., present parameters of the denoising model), for example, by backpropagating the loss through ANN 204 so as to force the network to fit its output (e.g., denoised image 208) to the target image (e.g., target denoised image 202b).

The training of ANN 204 may be repeated over multiple iterations and/or using additional paired images. For example, in an additional training iteration, ANN 204 may be configured to receive a second pair of training images that may include a second noisy source image and a second target denoised image. The second noisy source image may be the same as (or different from) the first noise source image (e.g., source image 202a) described above. The second target denoised image may include a different level of noise than the first target denoised image (e.g., target denoised image 202b). Responsive to receiving the second pair of training images, the level of noise included in the second target denoised image may be determined (e.g., using the techniques described above with respect to the first target denoised image). Based on the second source image and the determined noise level, ANN 204 may predict a denoised output image with a level of noise that approximates the determined noise level. ANN 204 may then compare the predicted denoised output image with the second target denoised image and determine a loss (e.g., difference) between the two images. The loss may be determined using one or more of the loss functions described herein and once determined, the loss may be used to further adjust the parameters of ANN 204 (e.g., parameters of the denoising model), for example, by backpropagating the loss through ANN 204 so as to force the network to fit its output to the second target denoised image.

Figure 3:
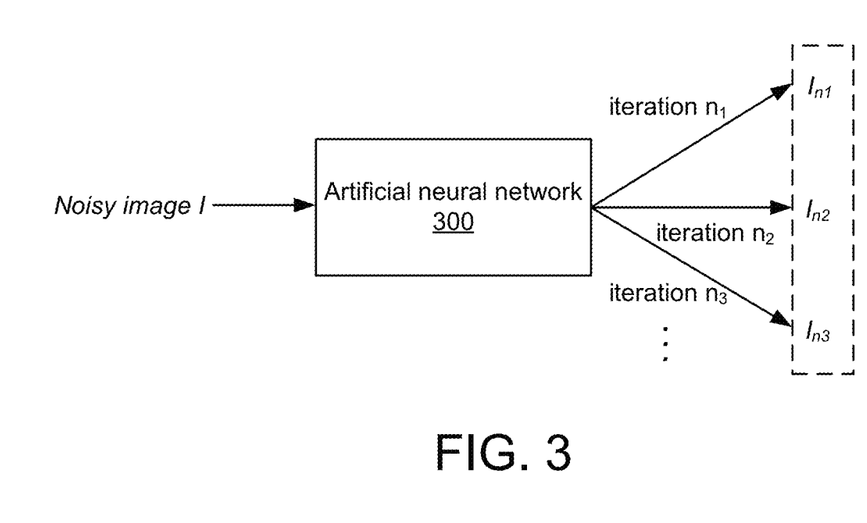
FIG. 3 is a diagram illustrating an example of using a second artificial neural network to generate target denoised images for training the artificial neural network of FIG. 1 or FIG. 2.

The images used to train ANN 204 such as the first and second target denoised images described above with respective noise levels may be generated using another artificial neural network. FIG. 3 illustrates an example of such an artificial neural network (e.g., ANN 300). As shown, ANN 300 may be a neural network configured to receive a noisy source input image I and generate a corresponding output image representing a denoised version of the input image. ANN 300 may be trained to acquire the ability to perform the denoising task over multiple iterations or steps, and during each iteration or step, ANN 300 may generate an output image (e.g., a denoised version of noisy source input image I) that may be an intermediate output image on way to obtain a final denoised image that satisfies the training goals. Since the difference between the noisy source input image and the denoised output image generated during each training iteration or step may decrease as the number of training iterations or steps increases, the intermediate output images generated by ANN 300 from the multiple iterations or steps may include respective (e.g., different) levels of noise (e.g., corresponding to different denoising strength). Accordingly, these intermediate output images (e.g., different denoised versions of noisy source input image I) may be used as target denoised images during the training of ANN 204, thus eliminating the need to obtain noise-free ground truth images. For example, during each training iteration $n_1$, $n_2$, $n_3$, etc. of ANN 300, the neural network may generate a respective intermediate output image $I_{n1}$, $I_{n2}$, $I_{n3}$, etc. that may include a corresponding level of noise (e.g., a certain signal-to-noise ratio (SNR)). These intermediate output images (e.g., $I_{n1}$, $I_{n2}$, $I_{n3}$, etc.) may be paired with the noisy source input image I (e.g., as paired images 202a and 202b shown in FIG. 2) and used to train the denoising neural network described herein (e.g., ANN 104 of FIG. 1 or ANN 204 of FIG. 2).

In examples, ANN 300 may include a convolutional neural network (CNN) such as a fully convolutional neural network that may be configured to, in response to receiving the noisy source input image I, predict a pixel value (e.g., for an output denoised image) based on one or more surrounding pixels. These surrounding pixels may be from a same input image (e.g., if a single static image is being denoised) or they may be from multiple adjacent images (e.g., if a series of spatial/temporal images such as those captured in a video is being denoised). The CNN may include multiple convolutional layers and/or one or more pooling layers. The convolutional layers may be followed by batch normalization and/or linear or non-linear activation (e.g., such as rectified linear unit or ReLU activation), and each of the convolutional layers may include a plurality of convolution kernels or filters having respective weights, the values of which may be learned through the training process described above so as to extract features from an input image. The features extracted by the convolutional layers may be downsampled through one or more pooling layers to obtain a representation of the features, for example, in the form of a feature map or feature vector. The CNN may further include one or more un-pooling layers and one or more transposed convolutional layers. Through the un-pooling layers, the CNN may up-sample the features extracted from the input images and further process the up-sampled features through the one or more transposed convolutional layers (e.g., via a plurality of deconvolution operations) to derive an up-scaled (e.g., dense) feature map or feature vector. The up-scaled feature map or vector may then be used to predict pixel values for an output image that may be free of certain noise.

In examples, deep learning techniques such as deep image prior (DIP) or a generative adversarial network (GAN) may be used to further improve the denoised output image (e.g., to refine the high-frequency details in the denoised output image). For instance, a dataset of cleaner medical images may be obtained from another imaging modality that is less constrained by imaging times, doses, and/or other factors (e.g., chest X-rays may be cleaner than cardiac X-ray fluoroscopy). Using such a cleaner dataset, another ANN may be trained (e.g., concurrently with the ANN described above such as ANN 204 of FIG. 2 and/or ANN 300 of FIG. 3) to discriminate if an image patch is cropped out from the output of ANN 204 (or ANN 300) or from the cleaner dataset of the other imaging modality. In the meanwhile, ANN 204 (or ANN 300) may be trained to make this discrimination task difficult such that the output images produced by ANN 204 (or ANN 300) may have a patch distribution close to that of the cleaner dataset (e.g., being sharper and cleaner). Using this strategy, cleaner images from one image modality (e.g., chest X-ray images) may be used to train an ANN (e.g., ANN 204 or 300) to denoise images produced by another imaging modality (e.g., cardiac X-ray fluoroscopy).

As described herein, the denoising neural network described herein such as ANN 104 of FIG. 1 and ANN 204 of FIG. 2 may have an encoder-decoder structure (e.g., a U-Net structure) with which multiple input images may be processed through respective input channels. Thus, in some examples, in addition to receiving a noisy input image such as noisy image 102 shown in FIG. 1 through a first input channel, the denoising neural network may receive a second image through a second input channel that represent a target noise level such as target noise level 106 shown in FIG. 1. Such a second image may be generated (e.g., by the denoising neural network) to have the same size as the noisy input image and each pixel in the second image may be assigned a value equal to the target noise level. The two images may then be processed via the respective first and second input channels to obtain a denoised output image. This way, the ANN may, through convolutional operations, access the target noise level when processing each pixel in the noisy input images. In examples, different pixels of the second image may be assigned different values, which may represent local target noise levels (e.g., local contrast to noise ratio (CNR)) in the noisy input image. Using this technique, the ANN may preserve details in high-contrast regions and/or smooth out the noise in low-contrast regions. The second image may be provided by a user or it may be predicted using another machine learning model.

In examples, to denoise multiple noisy input images (e.g., which may be parts of a video), the denoising neural network described herein (e.g., ANN 104 of FIG. 1 and ANN 204 of FIG. 2) may be configured to concurrently process multiple input images (e.g., utilize a U-Net structure) such that temporal information associated with the multiple input images may be used to improve the denoising performance. In examples, the denoising neural network described herein may include multiple serially connected sub-networks each having a U-Net structure to further optimize the denoised output image generated by the neural network. In examples, a noisy input image may be shuffled into multiple smaller noisy images, which may then be processed via respective input channels to further improve the denoising effects.

Figure 4:
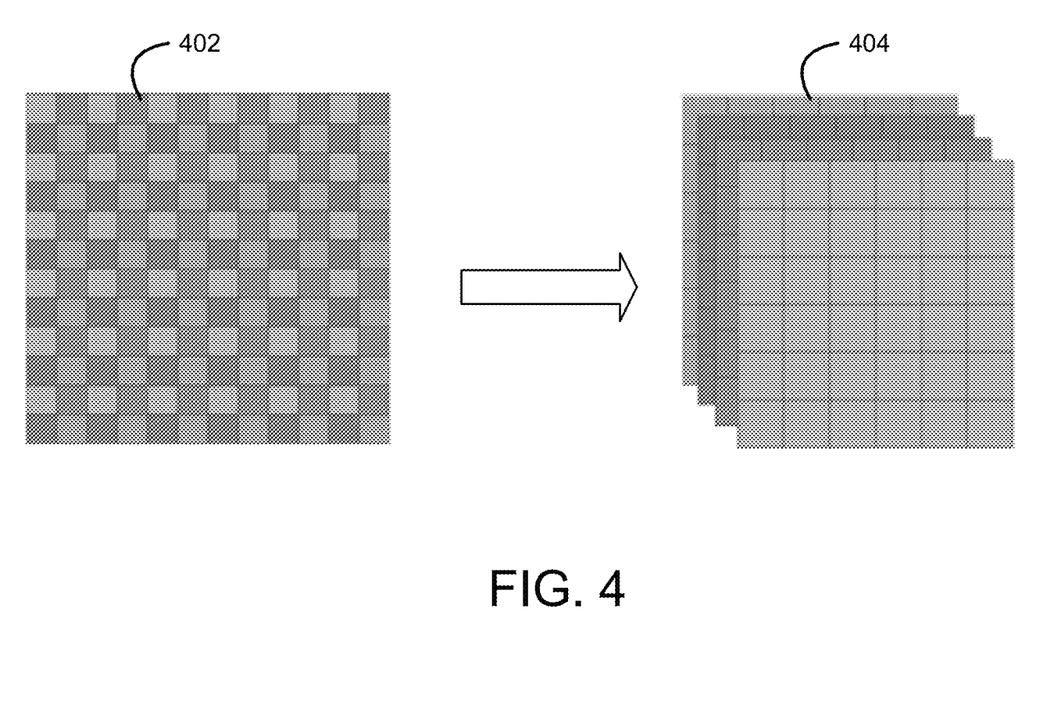
FIG. 4 is a diagram illustrating an example of shuffling an input noisy image to accomplish a faster denoising speed.

FIG. 4 illustrates an example of shuffling an input noisy image 402 into multiple smaller noisy images 404 to achieve a faster processing speed. For example, input noisy image 402 may have a size of 1024×1024 (e.g., in terms of pixels) and the denoising neural network described herein may have the ability to process multiple inputs through four input channels. As such, input image 402 may be shuffled into four smaller images each having a size of 512×512 (e.g., based on four input channels) before being provided to the denoising neural network described herein to achieve faster training and inference (e.g., by giving the neural network a larger sliding window or view of the image data) and/or better quality. The outputs produced by the neural network based on the shuffled images may then be shuffled back to the original size and/or shape.

Figure 5:
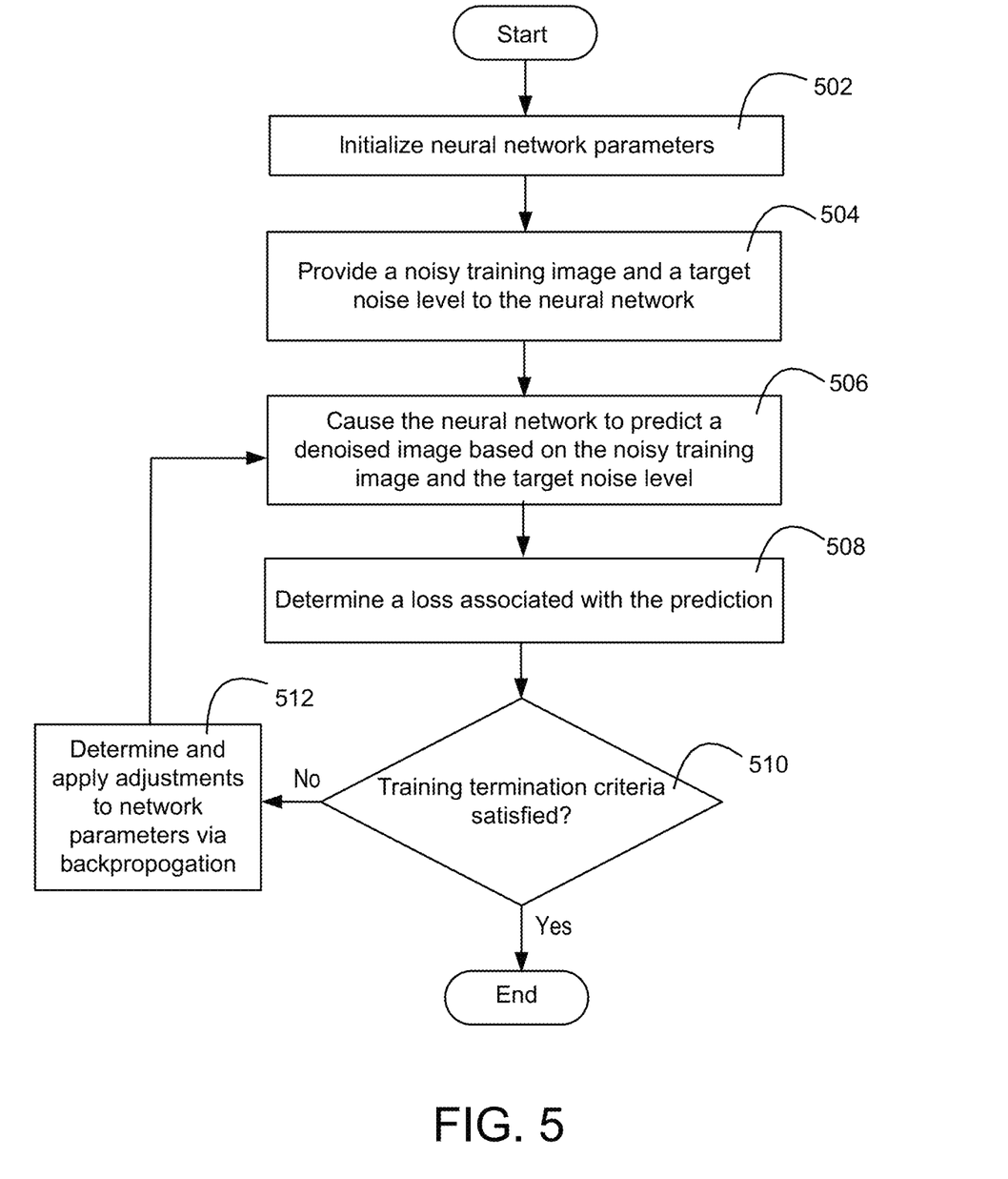
FIG. 5 is a flow diagram illustrating example operations that may be associated with training a neural network to perform the denoising tasks described herein.

FIG. 5 illustrates example operations that may be associated with training a neural network (e.g., ANN 104 of FIG. 1 or ANN 204 of FIG. 2) to perform the image denoising tasks described herein. As shown, the training operations may include initializing the parameters of the neural network (e.g., weights associated with the various filters or kernels of the neural network) at 502. The parameters may be initialized, for example, based on samples collected from one or more probability distributions or parameter values of another neural network having a similar architecture. The training operations may further include providing training data to the neural network at 504, and causing the neural network to predict a denoised image at 506. As described herein, the training data may include paired noisy medical images and target denoised images, which may be obtained based on the output(s) of a separate denoising neural network at different training steps or training iterations. From each of the target denoised images, a corresponding noise level may be determined and used to guide the prediction at 506. At 508, the denoised image predicted by the neural network may be compared with the target denoised image to determine a loss associated with the prediction. The loss may be determined using a suitable loss function such as, e.g., a loss function based on MSE, SSIM, etc. Once determined, the loss may be evaluated at 510 to determine whether one or more training termination criteria have been satisfied. For example, a training termination criterion may be deemed satisfied if the loss(es) described above is below a predetermined thresholds, if a change in the loss(es) between two training iterations (e.g., between consecutive training iterations) falls below a predetermined threshold, etc. If the determination at 510 is that a training termination criterion has been satisfied, the training may end. Otherwise, the loss may be backpropagated (e.g., based on a gradient descent associated with the loss) through the neural network at 512 before the training returns to 506.

For simplicity of explanation, the training steps are depicted and described herein with a specific order. It should be appreciated, however, that the training operations may occur in various orders, concurrently, and/or with other operations not presented or described herein. Furthermore, it should be noted that not all operations that may be included in the training process are depicted and described herein, and not all illustrated operations are required to be performed.

Figure 6:
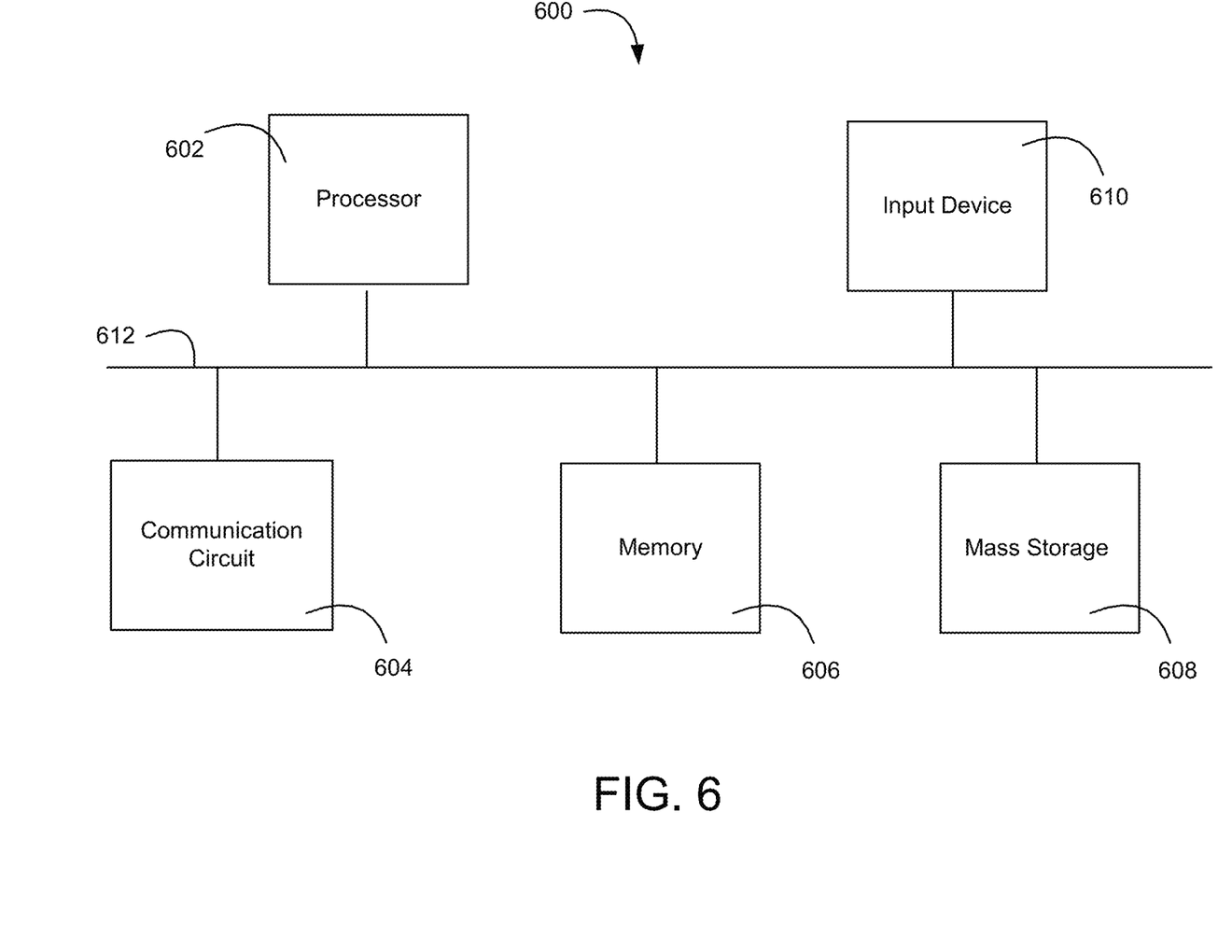
FIG. 6 is a block diagram illustrating example components of an apparatus that may be configured to perform one or more of the tasks described herein.

The systems, methods, and/or instrumentalities described herein may be implemented using one or more processors, one or more storage devices, and/or other suitable accessory devices such as display devices, communication devices, input/output devices, etc. FIG. 6 is a block diagram illustrating an example apparatus 600 that may be configured to perform the image denoising tasks described herein. As shown, apparatus 600 may include a processor (e.g., one or more processors) 602, which may be a central processing unit (CPU), a graphics processing unit (GPU), a microcontroller, a reduced instruction set computer (RISC) processor, application specific integrated circuits (ASICs), an application-specific instruction-set processor (ASIP), a physics processing unit (PPU), a digital signal processor (DSP), a field programmable gate array (FPGA), or any other circuit or processor capable of executing the functions described herein. Apparatus 600 may further include a communication circuit 604, a memory 606, a mass storage device 608, an input device 610, and/or a communication link 612 (e.g., a communication bus) over which the one or more components shown in the figure may exchange information.

Communication circuit 604 may be configured to transmit and receive information utilizing one or more communication protocols (e.g., TCP/IP) and one or more communication networks including a local area network (LAN), a wide area network (WAN), the Internet, a wireless data network (e.g., a Wi-Fi, 3G, 4G/LTE, or 5G network). Memory 606 may include a storage medium (e.g., a non-transitory storage medium) configured to store machine-readable instructions that, when executed, cause processor 602 to perform one or more of the functions described herein. Examples of the machine-readable medium may include volatile or non-volatile memory including but not limited to semiconductor memory (e.g., electrically programmable read-only memory (EPROM), electrically erasable programmable read-only memory (EEPROM)), flash memory, and/or the like. Mass storage device 608 may include one or more magnetic disks such as one or more internal hard disks, one or more removable disks, one or more magneto-optical disks, one or more CD-ROM or DVD-ROM disks, etc., on which instructions and/or data may be stored to facilitate the operation of processor 602. Input device 610 may include a keyboard, a mouse, a voice-controlled input device, a touch sensitive input device (e.g., a touch screen), and/or the like for receiving user inputs to apparatus 600.

It should be noted that apparatus 600 may operate as a standalone device or may be connected (e.g., networked, or clustered) with other computation devices to perform the functions described herein. And even though only one instance of each component is shown in FIG. 6, a skilled person in the art will understand that apparatus 600 may include multiple instances of one or more of the components shown in the figure.

While this disclosure has been described in terms of certain embodiments and generally associated methods, alterations and permutations of the embodiments and methods will be apparent to those skilled in the art. Accordingly, the above description of example embodiments does not constrain this disclosure. Other changes, substitutions, and alterations are also possible without departing from the spirit and scope of this disclosure. In addition, unless specifically stated otherwise, discussions utilizing terms such as "analyzing," "determining," "enabling," "identifying," "modifying" or the like, refer to the actions and processes of a computer system, or similar electronic computing device, that manipulates and transforms data represented as physical (e.g., electronic) quantities within the computer system's registers and memories into other data represented as physical quantities within the computer system memories or other such information storage, transmission or display devices.

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

What is claimed is:

1. An apparatus, comprising:
one or more processors configured to:
receive an input medical image comprising noise;
receive a target noise level; and
generate an output medical image using a first artificial neural network (ANN) such that at least a portion of the noise is removed from the output medical image in accordance with the target noise level, wherein the first ANN is trained to generate the output medical image in accordance with the target noise level through a training process and wherein, during the training process, the first ANN is configured to:
receive a first pair of training images that includes a first noisy training image and a first target training image, wherein the first target training image is generated using a second ANN and includes a first level of noise;
determine the first level of noise associated with the first target training image;
generate, using the first ANN, a denoised version of the first noisy training image based on the first level of noise; and
adjust parameters of the first ANN based on a difference between the denoised version of the first noisy training image and the first target training image.

2. The apparatus of claim 1, wherein, during the training process, the first ANN is further configured to:
receive a second pair of training images that includes a second noisy training image and a second target training image, wherein the second target training image is generated using the second ANN and includes a second level of noise;
determine the second level of noise associated with the second target training image;
generate, using the first ANN, a denoised version of the second noisy training image based on the second level of noise; and
adjust the parameters of the first ANN based on a difference between the denoised version of the second noisy training image and the second target training image.

3. The apparatus of claim 2, wherein the first noisy training image and the second noisy training image correspond to a same source image, and wherein the first level of noise is different than the second level of noise.

4. The apparatus of claim 3, wherein the first target training image and the second target training image are generated using the second ANN based on the source image.

5. The apparatus of claim 2, wherein the second ANN is pre-trained to denoise an input noisy image through multiple training iterations, during each of the multiple training iterations, the second ANN is configured to generate a respective intermediate denoised output image with a corresponding noise level based on the input noisy image, and wherein the first target training image is obtained as the intermediate denoised output image generated during a first training iteration of the second ANN and the second target training image is obtained as the intermediate denoised output image generated during a second training iteration of the second ANN.

6. The apparatus of claim 5, wherein the second ANN comprises a convolutional neural network (CNN) trained to predict a pixel value in an output image based on a corresponding pixel in the input noisy image and a plurality of pixels surrounding the corresponding pixel in the input noisy image.

7. The apparatus of claim 1, wherein the first ANN is configured to process multiple input images through respective input channels and wherein the one or more processors being configured to generate the output medical image using the first ANN comprises the one or more processors being configured to:
obtain an image having a same size as the input medical image, wherein each pixel of the image is assigned a value indicating the target noise level; and
process the obtained image and the input medical image via respective first input channel and second input channel of the first ANN.

8. The apparatus of claim 1, wherein the first ANN is configured to process multiple input images through respective input channels, and wherein the one or more processors being configured to generate the output medical image using the first ANN comprises the one or more processors being configured to shuffle the input medical image into a plurality of images each having a smaller image size than the input medical image and process the plurality of images through the respective input channels of the first ANN.

9. The apparatus of claim 1, wherein the target noise level corresponds to a target signal-to-noise ratio (SNR).

10. The apparatus of claim 1, wherein the input medical image comprises a fluoroscopic image.

11. A method of denoising medical images, the method comprising:
receiving an input medical image comprising noise;
receiving a target noise level; and
generating an output medical image using a first artificial neural network (ANN) such that at least a portion of the noise is removed from the output medical image in accordance with the target noise level, wherein the first ANN is trained to generate the output medical image in accordance with the target noise level through a training process and wherein, during the training process, the first ANN is configured to:
receive a first pair of training images that includes a first noisy training image and a first target training image, wherein the first target training image is generated using a second ANN and includes a first level of noise;
determine the first level of noise associated with the first target training image;
generate, using the first ANN, a denoised version of the first noisy training image based on the first level of noise; and
adjust parameters of the first ANN based on a difference between the denoised version of the first noisy training image and the first target training image.

12. The method of claim 11, wherein, during the training process, the first ANN is further configured to:
receive a second pair of training images that includes a second noisy training image and a second target training image, wherein the second target training image is generated using the second ANN and includes a second level of noise;
determine the second level of noise associated with the second target training image;
generate, using the first ANN, a denoised version of the second noisy training image based on the second level of noise; and
adjust the parameters of the first ANN based on a difference between the denoised version of the second noisy training image and the second target training image.

13. The method of claim 12, wherein the first noisy training image and the second noisy training image correspond to a same source image, and wherein the first level of noise is different than the second level of noise.

14. The method of claim 13, wherein the first target training image and the second target training image are generated using the second ANN based on the source image.

15. The method of claim 12, wherein the second ANN is pre-trained to denoise an input noisy image through multiple training iterations, during each of the multiple training iterations, the second ANN is configured to generate a respective intermediate denoised output image with a corresponding noise level based on the input noisy image, and wherein the first target training image is obtained as the intermediate denoised output image generated during a first training iteration of the second ANN and the second target training image is obtained as the intermediate denoised output image generated during a second training iteration of the second ANN.

16. The method of claim 11, wherein the first ANN is configured to process multiple input images through respective input channels and wherein generating the output medical image using the first ANN comprises:
    obtaining an image having a same size as the input medical image, wherein each pixel of the image is assigned a value indicating the target noise level; and
    processing the obtained image and the input medical image via respective first input channel and second input channel of the first ANN.

17. The method of claim 11, wherein the first ANN is configured to process multiple input images through respective input channels, and wherein generating the output medical image using the first ANN comprises shuffling the input medical image into a plurality of images each having a smaller image size than the input medical image and processing the plurality of images through the respective input channels of the first ANN.

18. The method of claim 11, wherein the target noise level corresponds to a target signal-to-noise ratio (SNR) and the input medical image comprises a fluoroscopic image.

19. A method of training a first artificial neural network (ANN) to denoise medical images, the method comprising:
    providing a first pair of training images to the first ANN, wherein the first pair of training images includes a noisy input training image and a first target training image, wherein the first target training image is generated using a second ANN from a first training iteration of the second ANN and includes a first level of noise;
    determine the first level of noise associated with the first target training image;
    generating, using the first ANN, a denoised version of the noisy input training image based on the first level of noise; and
    adjusting parameters of the first ANN based on a difference between the denoised version of the noisy input training image and the first target training image.

20. The method of claim 19, further comprising:
    providing a second pair of training images to the first ANN, wherein the second pair of training images includes the noisy input training image and a second target training image, wherein the second target training image is generated using the second ANN from a second training iteration of the second ANN and includes a second level of noise that is different than the first level of noise of the first target training image;
    determining the second level of noise associated with the second target training image;
    generating, using the first ANN, a denoised version of the noisy input training image based on the second level of noise; and
    adjusting the parameters of the first ANN based on a difference between the denoised version of the noisy input training image and the second target training image.

* * * * *